United States Patent [19]

Doggweiler et al.

[11] Patent Number: 4,973,722
[45] Date of Patent: Nov. 27, 1990

[54] PROCESS FOR PREPARING ORGANOMETALLIC COMPOUNDS

[75] Inventors: Hans O. Doggweiler, Möhlin; Vincent Desobry, Marly, both of Switzerland

[73] Assignee: Ciba-Geigy Corporation, Ardsley, N.Y.

[21] Appl. No.: 356,636

[22] Filed: May 22, 1989

Related U.S. Application Data

[63] Continuation of Ser. No. 118,093, Nov. 5, 1987, abandoned.

[30] Foreign Application Priority Data

Nov. 10, 1986 [CH] Switzerland ............... 4482/86

[51] Int. Cl.$^5$ .................... C07F 15/02; C07F 7/28
[52] U.S. Cl. ........................ 556/143; 556/53
[58] Field of Search ............... 556/143, 140, 53

[56] References Cited

U.S. PATENT DOCUMENTS

| | | | |
|---|---|---|---|
| 3,130,214 | 4/1964 | Coffield et al. | 556/13 |
| 3,190,902 | 6/1965 | Coffield et al. | 556/140 |
| 3,468,921 | 9/1969 | Wilke | 556/143 X |
| 3,960,911 | 6/1976 | Suschitzky et al. | 556/143 |
| 4,556,719 | 12/1985 | Boennemann et al. | 556/7 |

OTHER PUBLICATIONS

Chem. Abst. 100, 105179b.
V. H. Schumann, Chem. Zeitung 108, (7/8), 239, (1984).
V. H. Schumann, Chem. Zeitung 108, (11), 345, (1984).
A. N. Nesmeyanor et al., Koord. Khim. 1, 1252 (1975).
D. Astruc et al., Tetrahedron 32, 245, (1976).
Comparative Test Data Submitted to the EPO in EP 95,915.

Primary Examiner—Arthur C. Prescott
Attorney, Agent, or Firm—Luther A. R. Hall

[57] ABSTRACT

A process is described for preparing compounds of the formula I

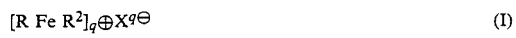

$$[R\ Fe\ R^2]_q \oplus X^{q\ominus} \qquad (I)$$

in which R is an anion of the formula $C_5H_4R^1$ or $C_9H_7$, $R^1$ is hydrogen, $C_1$–$C_6$-alkyl or halogen, $R^2$ is a $\pi$-arene, X is a q-valent anion and q is 1, 2, 3 or 4, by reacting ferrocene or a ferrocene derivative $(C_5H_4R^3)Fe(C_5H_4R^1)$ or $(C_9H_7)_2Fe$, in which $R^3$ has one of the meanings of $R^1$, with at least one mole of a $\pi$-arene $R^2$ in the presence of at least 1.4 moles, of a mixture of Al halide and Ti(IV) halide or $(C_5H_4R^1)$-Ti(IV) halide if desired in the presence of a metallic reducing agent, followed if desired by the replacement of the anion $X^{q-}$ in a manner known per se, with the proviso that the Lewis acid mixture contains at least 0.1 mole of Al halide and at least 0.1 mole of the Ti(IV) halide in question and that the indicated quantities are all based on one mole of the ferrocene (derivative).

The process is suitable, if suitable amounts of reactants are chosen, for simultaneously preparing compounds of the formula I and titanocene dihalides.

25 Claims, No Drawings

PROCESS FOR PREPARING ORGANOMETALLIC COMPOUNDS

This is a continuation of application Ser. No. 118,093, filed Nov. 5, 1987, now abandoned. The present invention relates to an improved process for preparing organometallic compounds, in particular iron-arene complexes, by ligand exchange reaction on ferrocene (derivatives). Iron-arene complexes and the use thereof as photoinitiators for cationically polymerizable materials are known and described for example in EP-A-94,915. In general, the compounds are prepared from metallocene compounds by ligand exchange reactions. To this end, the metallocene compound, for example ferrocene, is reacted with an aromatic compound in the presence of a Lewis acid and Al metal.

The preparation of cyclopentadiene-iron-arene compounds is described for example in Chemiker Zeitung 108 (7/8), 239 (1984) and 108 (11), 345 (1984). Further examples of these reactions are found in Koord. Khim., 1, 1252 (1975). The Lewis acids used therein include Al halides. According to this last publication, not all Lewis acids are suitable for the ligand exchange reaction on ferrocene; $TiCl_4$, in particular, is considered unsuitable.

EP-B-94,915 discloses that $TiCl_4$ combined with Al metal can be used for the ligand exchange reaction on ferrocene derivatives. It has now been found that the ligand exchange reaction can be designed in very high yields with the combination of Ti halide/Al halide in such a way that lower reaction temperatures and at the same time higher reaction rates are obtainable. Furthermore, in some cases it is possible to obtain two useful organometallic compounds at the same time through careful choice of the amounts of reactants.

Effectively, the property of the Ti(IV) halide to act as an acceptor for the displaced cyclopentadiene (derivative) is exploited, producing in the cases mentioned an isolatable reaction product. If the ligand exchange is carried out with $AlCl_3$, the leaving cyclopentadiene (derivatives) generally form polymeric products (cf. D. Astruc et al. in Tetrahedron, 32, 245–249 (1976)).

The present invention relates to a process for preparing compound of the formula I

in which R is an anion of the formula $C_5H_4R^1$ or $C_9H_7$, $R^1$ is hydrogen, $C_1$–$C_6$-alkyl or halogen, $R^2$ is a $\pi$-arene, X is a q-valent anion and q is 1, 2, 3 or 4, by reacting ferrocene or a ferrocene derivative $(C_5H_4R^3)Fe(C_5H_4R^1)$ or $(C_9H_7)_2Fe$, in which $R^3$ has one of the meanings of $R^1$, with at least one mole of a $\pi$-arene $R^2$ in the presence of at least 1.4 moles, preferably at least 1.5 moles, of a mixture of Al halide and Ti(IV) halide or $(C_5H_4R^1)$-Ti(IV) halide if desired in the presence of a metallic reducing agent, followed if desired by the replacement of the anion $X^{q-}$ in a manner known per se, with the proviso that the Lewis acid mixture contains at least 0.1 mole of Al halide and at least 0.1 mole of Ti(IV) halide or of $(C_5H_4R^1)$-Ti(IV) halide and that the indicated quantities are all based on one mole of the ferrocene (derivative). q is preferably 1 or 2, particularly preferably 1. R is an indenyl anion $C_9H_7$ or preferably a cyclopentadienyl anion $C_5H_4R^1$.

$C_1$–$C_6$-alkyls $R^1$ and $R^3$ are straight-chain or branched, preferably straight-chain. Examples of radicals of this type are methyl, ethyl, n-propyl, isopropyl, n-butyl, n-pentyl and n-hexyl. Preference is given to methyl.

Halogens $R^1$ and $R^3$ are fluorine, chlorine, bromine or iodine. Preference is given to chlorine.

$R^1$ and $R^3$ are preferably hydrogen or methyl, very particularly preferably hydrogen.

A $\pi$-arene $R^2$ is in particular an aromatic group having 6 to 24 carbon atoms or a heteroaromatic group having 3 to 30 carbon atoms and one or two heteroatoms, it being possible for these groups to be monosubstituted or polysubstituted by identical or different monovalent radicals such as halogen atoms, preferably chlorine or bromine atoms, or $C_1$–$C_8$-alkyl, $C_1$–$C_8$-alkoxy, cyano, $C_1$–$C_8$-alkylthio, $C_2$–$C_6$-monocarboxylic alkyl ester or phenyl groups. These $\pi$-arene groups can be monocyclic, fused polycyclic or non-fused polycyclic aromatic hydrocarbons, the rings in the lastmentioned systems possibly being linked directly or via bridge members such as —S— or —O—.

Suitable heteroaromatic $\pi$-arenes are systems which preferably contain one or two S and/or O atoms.

Examples of suitable $\pi$-arenes are benzene, toluene, xylenes, ethylbenzene, cumene, methoxybenzene, ethoxybenzene, dimethoxybenzene, p-chlorotoluene, m-chlorotoluene, chlorobenzene, bromobenzene, dichlorobenzene, diisopropylbenzene, trimethylbenzene, naphthalene, 1,2-dihydronaphthalene, 1,2,3,4-tetrahydronaphthalene, methylnaphthalene, methoxynaphthalene, ethoxynaphthalene, chloronaphthalene, bromonaphthalene, dimethylnaphthalene, biphenyl, stilbene, indene, 4,4'-dimethylbiphenyl, fluorene, phenanthrene, anthracene, 9,10-dihydroanthracene, triphenyl, pyrene, perylene, naphthacene, coronene, thiophene, chromene, xanthene, thioxanthene, benzofuran, benzothiophene, naphthothiophene, thianthrene, diphenylene oxide and diphenylene sulfide.

X can be any desired q-valent anion of an inorganic or organic acid, for example a halide, i.e. fluoride, chloride, bromide or iodide, or a pseudohalide, for example cyanide, cyanate or thiocyanate, or an anion of other inorganic acids, for example sulfate, phosphate, nitrate, perchlorate or tetraphenylborate.

Further suitable anions are derived from sulfonic acids of aliphatic or aromatic compounds. Preferred examples thereof are p-toluenesulfonate, p-trifluoromethylbenzenesulfonate and trifluoromethylsulfonate.

Particular preference is given to non-nucleophilic anions $X^{q-}$.

Suitable non-nucleophilic anions $X^{q-}$ are in particular anions of the formula II

in which L is a di- to heptavalent metal or non-metal, Q is a halogen atom or, if L is phosphorus, arsenic or antimony and m is 5, can also be OH, q is 1, 2, 3 or 4 and m is an integer corresponding to the valency of L +q.

Examples of such anions are $BF_4^-$, $AlF_4^-$, $AlCl_4^-$, $TiF_6{}^{2-}$, $PF_y^-$, $SbF_6^-$, $SbCl_6^-$, $SbI_6^-$, $SbF_5(OH)^-$, $GeF_6^-$, $ZrF_6{}^{2-}$, $AsF_6^-$, $FeCl_4^-$, $SnF_6{}^2$, $SnCl_6{}^{2-}$ and $BiCl_6^-$. Preferred examples of complex anions are $BF_4^-$, and in particular $AsF_6^-$, $SbF_6$ and $PF_6^-$.

Further suitable non-nucleophilic anions are derived from heteropoly acids. Examples of anions of this type are phosphorotungstenate ($PO_{40}W_{12}{}^{3-}$) and silicotungstenate ($SiO_{40}W_{12}{}^{4-}$).

The Al or Ti(IV) halides defined above include the corresponding Al-trihalides or Ti-(IV)-tetrahalides, such as the chlorides, bromides and iodides. Preference is given to using the chlorides and bromides, but in particular the chlorides.

It is also possible to use cyclopentadienyl-Ti(IV) trihalides. Preference is given to using Ti(IV) halides.

Cyclopentadienyl-Ti(IV) trihalides can be obtained in a manner known per se by reacting the corresponding Ti(IV) halides with alkali metal cyclopentadienyls.

Preferred Ti(IV) halides are $TiBr_4$ and in particular $TiCl_4$.

The preferred total amount of Lewis acid is 1.5–6.0 moles, preferably 1.5–2.5 moles, in particular 1.6–2.0 moles, very particularly preferably 1.7–1.9 moles, based on one mole of ferrocene (derivative).

The molar ratio of Ti(IV) halide : Al halide is preferably 1:4 to 4:1, but in particular 1:2 to 1:3. Preference is given to a process wherein a mixture of Al halide and Ti(IV) halide is used.

In a preferred embodiment, the amount of Ti(IV) halide is 0.6–1.9 moles, based on one mole of ferrocene (derivative); if desired, a metallic reducing agent is used in this variant.

Particular preference is given to a process variant wherein a mixture of 0.1–4.0 moles, very particularly 2.0–3.0 moles, of Al halide and 0.7–1.9 moles, very particularly 0.9–1.1 moles, of Ti(IV) halide, based on one mole of ferrocene (derivative) is used, if desired, in the presence of finely divided Al, very particularly 0.3–0.4 mole, the halide being bromide or chloride.

Similar preference is given to a process variant wherein a mixture of 1.5–2.0 moles of $AlCl_3$ and 0.9–1.1 moles of $(C_5H_5)TiCl_3$ is used together with 0.3–0.4 mole of finely divided Al, based on one mole of ferrocene (derivative).

The embodiment wherein Ti(IV) halide/Al halide mixture containing 0.3–0.7 mole, preferably 0.4–0.6 mole, very particularly preferably about 0.5 mole, of Ti(IV) halide, based on one mole of ferrocene (derivative), is used, is particularly preferred since this way of carrying out the process produces in addition to the metallocene derivative of the formula I the product of the formula III

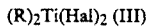

$(R)_2Ti(Hal)_2$ (III)

in which R is as defined above, preferably $C_5H_4R^1$, and Hal is a halogen atom.

Compounds of the formula III, in particular $(C_5H_5)_2TiCl_2$, are useful intermediates and can be used for example for preparing titanocene initiators. These compounds and their use as photoinitiators for the polymerization of ethylenically unsaturated compounds are described in EP-A-122,223.

In the above variant, the property of the Ti(IV) halide of acting as a cyclopentadienyl acceptor is exploited. The cyclopentadienyl (derivative) replaced in the ferrocene (derivative) is thus transferred to the Ti(IV) halide.

In this variant, the molar ratio of Al halide : Ti(IV) halide is advantageously 2:1 or greater than 2:1. In the absence of a metallic reducing agent, it is also possible to use a smaller amount of Al halide, for example a molar ratio of 1:1.

Amounts of Ti(IV) halide far in excess of stoichiometric amounts have to be avoided in this process variant since, otherwise, polymeric by-products can form, thereby reducing the yield of $(Cpd)_2TiHal_2$ [Cpd =cyclopentadienyl anion], which can lead to difficulties in the work-up (filtration).

Preferably, this process variant is carried out with a mixture of 0.3–0.7 mole of Ti(IV) halide and 0.8–2.0 moles of Al halide, based on one mole of ferrocene (derivative), in the presence if desired of finely divided Al, halide being bromide or chloride.

Particularly preferably, this process variant is carried out with a mixture of 0.4–0.6 mole of Ti(IV) halide and 1.0–1.8 moles of Al halide, if desired in the presence of 0.1–1.0 mole of finely divided Al, based on one mole of ferrocene (derivative), halide being bromide or chloride.

In a further very particularly preferred embodiment of the process, use is made of a mixture of 0.4–0.6 mole, preferably about 0.5 mole, of $TiCl_4$ and 1.2–1.4 moles, preferably 1.3–1.35 moles, of $AlCl_3$ if desired in the presence of 0.15–0.2 mole of finely divided Al, based on one mole of ferrocene (derivative).

The metallic reducing agent can be for example magnesium, zinc or aluminium. Aluminium is particularly preferred.

The presence of a metallic reducing agent is more or less important, depending on the mixing ratios of the reactants.

If the variant where about 0.3–0.7 moles of Ti(IV) halide, based on one mole of ferrocene (derivative), is used, the yield of compound of the formula I is in general not critically affected by the presence of a metallic reducing agent. However, by adding a metallic reducing agent it is in general possible to increase the purity of the products.

The fact that the reaction can also be carried out without a metal being added is particularly surprising since, if $TiCl_4$ is present as the only Lewis acid, no compound of the formula I is obtainable in the absence of Al metal (cf. also Koord. Khim., 1, 1252 (1975)).

If the reaction is carried out with a superstoichiometric or a substoichiometric amount of Ti(IV) halide, it is advisable to add a metallic reducing agent to increase the yields. This metallic reducing agent can be used in any desired amounts; preferably, however, more than 0.1 mole, particularly preferably 0.1–1.0 mole, based on one mole of ferrocene (derivative), should be used.

Very particularly preferably the metallic reducing agent is present in an equivalent amount relative to the Ti(IV) halide. In the case of an Al, it is thus preferable to use a third of the molar amount of Ti(IV) halide.

The metal should be used in a form which offers a large surface area. For instance, it can be added for example as a foil or in finely divided form, preferably as a powder or as a dust.

The π-arene can be used in any desired excess, for example as solvent. However, at least 1 mole, based on one mole of ferrocene (derivative), should be introduced at the beginning. It is also possible to use mixtures of π-arenes.

The reaction may be carried out in a further solvent. It is possible to use any solvent which is inert under the reaction conditions. The basisity of this solvent should not be so high as to excessively deactivate the Lewis acid(s). Examples of suitable solvents are (cyclo)aliphatic or aromatic hydrocarbons which can carry nonbasic substituents, for example halogen atoms or alkyl groups. Preference is given to $C_6$–$C_{12}$-hydrocarbons. Examples of preferred solvents of this kind are n-hexane, n-heptane, n-octane, n-nonane, n-decane, n-undecane, n-dodecane and corresponding branched representatives of these types; it is also possible to use mixtures of aliphatic hydrocarbons, for example the octane fraction. The preferred cycloaliphatic solvent is methylcyclohexane. The aliphatic hydrocarbons can be chlorinated. Further preferred solvents are benzene, toluene, xylene, ethylbenzene, cumene, chlorobenzene and dichlorobenzene.

Preferably, no additional solvent is used and the $\pi$-arene $R^2$ is used in an amount of 2.0–10.0 moles, based on one mole of ferrocene (derivative).

The reaction mixture can contain small amounts of water, for example 0.1–2% by weight, based on the amount of Lewis acid, as described for the case of $AlCl_3$ being used as Lewis acid in Koord. Khim., 1, 1252 (1975).

The ferrocene (derivative) is preferably ferrocene. However, it is also possible to use any desired derivatives which have substituted cyclopentadienyl anions or indenyl anions. Examples of such derivatives are bis-indenyl-iron(II), chloroferrocene, dichloroferrocene, methylferrocene and dimethylferrocene. Preference is given to using ferrocene and the readily accessible monosubstituted ferrocene derivatives, but in particular ferrocene.

The reaction is advantageously carried out within the temperature range of 15°–250° C. The preferred temperature range is 50°–150° C.

The reaction time is in general 0.25–24 hours, depending on the temperature. Preferably, it is 1–2 hours.

The process can be carried out in the air or under a protective gas. Advantageously, it is carried out in the absence of oxygen, for example under nitrogen or under argon.

All the educts can be introduced together at the beginning, and the reaction can be initiated if necessary by heating. In some cases, however, it is proven advantageous to add individual reactants during the reaction. For instance, $TiCl_4$, for example, can be added dropwise during the reaction to control the reaction rate and hence also the heat of reaction.

After the reaction has ended, the reaction mixture is in general deactivated with water or ice-water which may be acidified. Thereafter the mixture is in general filtered to separate off Al metal or undissolved reaction constituents. In certain circumstances, phase separation would also be necessary. The aqueous phase obtained may then be extracted with a polar, organic solvent, for example with chloroform or dichloromethane, to remove unconverted compounds or useful by-products. This extraction stage is of particular interest in the case of the reaction variant where $R_2TiHal_2$ is formed at the same time. In this case, deactivation is effected with acidified water or ice-water, and filtration and phase separation are followed by an extraction under oxidative conditions, for example in air.

However, the $R_2TiHal_2$ can also be precipitated by oxidative treatment of the reaction mixture deactivated with acidified water or ice-water, and then be filtered off. To this end, the deactivated reaction mixture is treated for example with atmospheric oxygen or with other oxidizing agents, for example with $H_2O_2$.

The compound of the formula I is initially obtained in the form of the halide. This halide is, if desired, isolated and purified in a manner known per se, for example by recrystallization, or other anions are introduced in a manner known per se in the course of working up the reaction mixture. For instance, an acid or a water-soluble salt of said acid can be added for example to the isolated aqueous phase to precipitate the compound of the formula I in this way.

Examples of suitable precipitants are the Na or K salts and the free acids of the anions listed above as preferred.

These anions can also be introduced in a manner known per se by means of ion exchange.

Compounds of formula I with non-nucleophilic anions can be used as photoinitiators for cationically polymerisable materials. Compounds of formula I with nucleophilic anions can be used for preparing these photoinitiators in the manner described above.

The examples which follow illustrate the invention:

EXAMPLE 1:

($n^6$-cumene)-($n^5$-cyclopentadienyl)-iron(II) hexafluorophosphate and titanocene dichloride.

47.4 g (0.25 mol) of titanium tetrachloride are added dropwise under nitrogen at 25° C. in the course of 30 minutes to a mixture of 600 g (5 mol) of cumene, 93 g (0.5 mol) of ferrocene, 6.8 g (0.25 mol) of aluminium dust and 66.8 g (0.5 mol) of aluminium chloride. The reaction mixture is stirred at 100° C. for 1 hour, then cooled to below 30° C. and poured onto 1500 g of 6% hydrochloric acid. Excess aluminium is filtered off, and the organic phase is separated off. The aqueous phase is extracted with 800 g of chloroform in three portions to remove titanocene dichloride (yield: 24 g =39% of theory; melting point: 260° C.). 92 g (0.5 mol) of potassium hexafluorophosphate are added to the aqueous phase, and the precipitated (q6-cumene)-(q5-cyclopentadienyl)iron(II) hexafluorophosphate is filtered off, washed and dried. Yield: 137 g (71% of theory); melting point: 85° C.

EXAMPLE 2:

($n^6$-cumene)-($n^5$-cyclopentadienyl)-iron(II) hexafluorophosphate and titanocene dichloride.

37.9 g (0.2 mol) of titanium tetrachloride are added dropwise under nitrogen at 60° C. in the course of 30 minutes to a mixture of 300 g (2.5 mol) of cumene, 74.4 g (0.4 mol) of ferrocene, 1.8 g (0.07 mol) of aluminium powder and 71.2 g (0.53 mol) of aluminium chloride. The reaction mixture is stirred at 100° C. for 1 hour, then cooled to below 25° C. and poured onto an inertized mixture of 650 g of ice and 150 g of 32% hydrochloric acid. Titanocene dichloride is precipitated by oxidation with 11.3 g (0.1 mol) of 30% hydrogen peroxide and then filtered off (yield: 44.9 g (90.2% of theory); melting point: 280° C.). After phase separation, 81 g (0.44 mol) of potassium hexafluorophosphate are added as an aqueous solution to the aqueous phase, after which the precipitated ($n^6$-cumene)-($n^5$-cyclopentadienyl)-iron(II) hexafluorophosphate is filtered off, washed and dried. Yield: 134 g (86.6% of theory); melting point: 86° C.

EXAMPLE 3:

($n^6$-cumene)-($n^5$-cyclopentadienyl)-iron(II) hexafluorophosphate and titanocene dichloride (reaction with cyclopentadienyl-Ti(IV) trichloride)

Example 2 is repeated: 32.9 g (0.15 mol) of cyclopentadienyl-titanium trichloride are added under nitrogen at 60° C. in the course of 30 minutes to a stirred mixture of 129.3 g (1.265 mol) of cumene, 27.9 g (0.15 mol) of ferrocene, 33.2 g (0.249 mol) of aluminium chloride and 1.35 g (0.0495 mol) of aluminium powder. The reaction mixture is stirred at 100° C. for 1.5 hours, then cooled to below 25° C. and worked up in a manner similar to Example 2. This gives 20.2 g of crude titanocene dichloride (54.2% of theory) which is purified further by sublimation and 40 g of (n⁶cumene)-(n⁵-cyclopentadienyl)-iron(II) hexafluorophosphate (69.1% of theory; melting point: 85° C.).

| Elemental analysis | % C | % H |
|---|---|---|
| [(Cumene)Fe(Cpd)]PF₆ calculated | 43.55 | 4.44 |
| found | 43.79 | 4.47 |
| Cpd₂TiCl₂ calculated | 48.24 | 4.05 |
| (sublimed) found | 48.26 | 4.11 |

EXAMPLE 4:
(n⁶-cumene)-(n⁵-cyclopentadienyl)-iron(II) hexafluorophosphate Example 2 is repeated using the stoichiometry (all amounts in mol) ferrocene/AlCl₃/Al/TiCl₄/cumene: 1/1.66/ 0.33/1/10. A 90.05% yield is obtained of (n⁶-cumene)-(n⁵-cyclopentadienyl)-iron(II) hexafluorophosphate having a melting point of 83°–85° C.

| Elemental analysis | % C | % H |
|---|---|---|
| calculated | 43.55 | 4.44 |
| found | 43.61 | 4.44 |

EXAMPLE 5

Example 4 is repeated, except that the stoichiometry (all amounts in mol) ferrocene/AlCl₃Al/TiCl₄/cumene: 1/2.66/0.33/1/10 affords a 93.74% yield of (n⁶-cumene)-(n⁵-cyclopentadienyl)-iron(II) hexafluorophosphate 93.74%; melting point 82°–84° C.

| Elemental analysis | % C | % H |
|---|---|---|
| calculated | 43.55 | 4.44 |
| found | 43.34 | 4.47 |

EXAMPLES 6–17: General method

Ferrocene is reacted with the particular arene, AlCl₃/TiCl₄ mixture, Al powder in the absence or presence of solvent as specified in Table I below. The work-up is carried out as described in Example 2 by deactivation in ice/hydrochloric acid, optional isolation of titanocene dichloride, phase separation and precipitation of the iron compound with potassium hexafluorophosphate. The analytical data of the compounds obtained can be found in Table II.

TABLE I

Overview of conducted experiments

| Example No. | Product | Ferrocene (mol) | Arene (mol) | AlCl₃ (mol) | TiCl₄ (mol) | Al powder (mol) | Solvent (mol) | Yield Fe compound (% of theory) | Yield Cp₂TiCl₂ (% of theory) |
|---|---|---|---|---|---|---|---|---|---|
| 6 | η⁶-Biphenyl-η⁵-cyclopentadienyl-iron(II) hexafluorophosphate | 1 | 5 | 1 | 0.5 | 0.5 | Methyl-cyclohex-ane (8) | crude: 72.3 cryst-alline: 64.1 | (¹) |
| 7 | η⁶-(1,3-dimethylbenzene)-η⁵-cyclopentadienyl-iron(II) hexafluorophosphate | 1 | 8 | 1 | 0.5 | 0.5 | — | crude: 78 cryst-alline: 74 | (¹) |
| 8 | η⁶-(1,3,5-trimethylbenzene)η⁵-cyclopentadienyl-iron(II) hexafluorophosphate | 1 | 7.2 | 1 | 0.5 | 0.5 | — | crude: 80.3 cryst-alline: 60 | (¹) |
| 9 | η⁶-naphthalene-η⁵-cyclopentadienyl-iron(II) hexafluorophosphate | 1 | 4 | 1 | 0.5 | 0.5 | Methyl-cyclohex-ane (8) | crude: 79.1 cryst-alline: 66.2 | (¹) |
| 10 | η⁶-1-methylnaphthalene-η⁵-cyclopentadienyl-iron(II) hexafluorophosphate | 1 | 4 | 1 | 0.5 | 0.5 | Methyl-cyclohex-ane (8) | crude: 84.1 cryst-alline: 73.5 | (¹) |
| 11 | η⁶-1-methylnaphthalene-η⁵-cyclopentadienyl-iron(II) hexafluorophosphate | 1 | 6.3 | 1.33 | 0.5 | 0.166 | — | crude: 81.3 | 45.5 |
| 12 | η⁶-2-methylnaphthalene-η⁵-cyclopentadienyl-iron(II) hexafluorophosphate | 1 | 4 | 1 | 0.5 | 0.5 | Methyl-cyclohex-ane (8) | crude: 69 cryst-alline: 59.8 | (¹) |
| 13 | η⁶-toluene-η⁵-cyclopentadienyl-iron(II) hexafluorophosphate | 1 | 10 | 1.33 | 0.5 | 0.166 | — | crude: 87 | 78.3 |
| 14 | η⁶-(1,4-dimethylbenzene)-η⁵-cyclopentadienyl-iron(II) hexafluorophosphate | 1 | 7 | 1.33 | 0.5 | 0.166 | — | crude: 88.4 | 30.5 |
| 15 | η⁶-(1,3-di-isopropylbenzene)-η⁵-cyclopentadienyl-iron(II) hexafluorophosphate | 1 | 6 | 1.33 | 0.5 | 0.166 | — | crude: 83.1 | 68.8 |
| 16 | η⁶-cumene-η⁵-methylcyclopentadienyl-iron(II) hexafluorophosphate | 1 (²) | 6.3 | 1.33 | 0.5 | 0.166 | — | crude: 81.3 | 36.2 (⁴) |
| 17 | η⁶-1-cumene-η⁵-indenyl-iron(II) hexafluorophosphate | 1 (³) | 10 | 1.33 | 0.5 | 0.166 | — | cryst-alline: 70.6 | — |

(¹) Not isolated
(²) Ferrocene replaced by bis-methylcyclopentadienyliron(II).
(³) Ferrocene replaced by bis-indenyliron(II).
(⁴) Bis-(methylcyclopentadienyl)-titanium(IV) dichloride is formed.

TABLE II

Analytical data on compounds obtained according to Examples 6-17

| Example No. | Elemental analysis of iron compound | | | Melting point of iron compound (°C.) | Elemental analysis of titanium compound | | | Melting point of titanium compound |
|---|---|---|---|---|---|---|---|---|
| | | % C | % H | | | % C | % H | % Cl | |
| 6 | calculated: | 48.60 | 3.60 | 139-141 | | (²) | | | (²) |
| | found: | 48.54 | 3.58 | | | | | | |
| 7 | calculated: | 41.97 | 4.06 | 265-270 (decomposition) | | (²) | | | (²) |
| | found: | 41.9 | 4.07 | | | | | | |
| 8 | calculated: | 43.55 | 4.44 | 290-294 | | (²) | | | (²) |
| | found: | 43.48 | 4.46 | | | | | | |
| 9 | calculated: | 45.72 | 3.32 | 170-175 | | (²) | | | (²) |
| | found: | 45.17 | 3.52 | | | | | | |
| 10 | calculated: | 47.09 | 3.70 | 155-158 | | (²) | | | (²) |
| | found: | 46.81 | 3.67 | | | | | | |
| 11 | | (¹) | | (³) | | (¹) | | | (¹) |
| 12 | calculated: | 47.09 | 3.70 | 155-159 | | (²) | | | (²) |
| | found: | 47.11 | 3.74 | | | | | | |
| 13 | calculated: | 40.26 | 3.66 | 240-270 | calculated: | 48.24 | 4.05 | 28.48 | 240-270 |
| | found: | 40.12 | 3.66 | | found: | 47.37 | 4.21 | 27.7 | |
| 14 | calculated: | 41.85 | 4.32 | 180 (decomp.) | | (¹) | | | (¹) |
| | found: | 41.70 | 4.12 | | | | | | |
| 15 | calculated: | 47.69 | 5.41 | 85-91 | calculated: | 48.24 | 4.05 | 28.48 | 220-260 |
| | found: | 47.39 | 5.37 | | found: | 49.56 | 4.55 | 26.03 | |
| 16 (⁴) | | (¹) | | (¹) | calculated: | 52.05 | 5.09 | 25.59 | (¹) |
| (⁵) | | | | | found: | 52.03 | 5.10 | 24.94 | |
| 17 | calculated: | 49.57 | 4.39 | (¹) | | (²) | | | (²) |
| | found: | 49.88 | 4.36 | | | | | | |

(¹) Not carried out.
(²) Not isolated.
(³) ¹H-NMR spectrum of iron compound (δ values against TMS): 2.54; 4.5; 6.2-6.35; 7.03-7.2; 7.6-8.05 ppm (100 MHz spectrometer)
(⁴) ¹H-NMR spectrum of iron compound (δ values against TMS): 1.33; 1.40; 2.06; 4.97; 6.28 ppm (100 MHz spectrometer)
(⁵) ¹H-NMR spectrum of titanium compound (δ values against TMS): 2.33; 6.25-6.5 ppm (100 MHz spectrometer)

What is claimed is:

1. A process for preparing a compound of formula I

$$[R \; Fe \; R^2]_q^{\oplus} X^{q\ominus} \qquad (I)$$

R is an anion of the formula $C_5H_4R^1$- or $C_9H_7$-,
$R^1$ and $R^3$ are independently hydrogen, $C_1-C_6$-alkyl or halogen,
$R^2$ is a pi-arene,
X is a q-valent anion, and
q is 1, 2, 3 or 4,
with the proviso that when Q>1, $R^2$ is the same pi-arene in each $[R \; Fe \; R^2 \; \pi_q+$, which comprises reacting ferrocene, $(C_5H_4R^3-)Fe(C_5H_4R^1-)$ or $(C_9H_7-)_2Fe$ with at least one mole of pi-arene $R^2$ in the presence of at least 1.4 moles of a mixture of Al halide and Ti(IV) halide or $(C_5H_4R^1-)$—Ti(IV) halide, with the proviso that the mixture contains at least 0.1 mole of Al halide and at least 0.1 mole of Ti(IV) halide or of $(C_5H_4R^1-)$—Ti(IV) halide, with all indicated quantities based on one mole of ferrocene, $(C_5H_4R^3-)Fe(C_5H_4R^1-)$ or $(C_9H_7-)_2$ Fe.

2. A process according to claim 1, wherein R is a cyclopentadienyl anion $C_5H_4R^1$ and $R^1$ is hydrogen or methyl.

3. A process according to claim 36, wherein $R^1$ is hydrogen.

4. A process according to claim 1, wherein the π-arene $R_2$ to an aromatic group having 6 to 24 carbon atoms or a heteroaromatic group having 3 to 30 carbon atoms and one or two heteroatoms.

5. A process according to claim 1, wherein X is selected from the group consisting of $BF_4-$, $PF_6-$, $AsF_6-$ and $SbF_6-$.

6. A process according to claim 1, wherein 1.5-6.0 moles of Lewis acid, based on one mole of ferrocene, $(C_5H_4R^3-)$, $Fe(C_5H_4R^1-)$ or $(C_9H_7-)_2$ Fe, are used.

7. A process according to claim 1, wherein the molar ratio of Ti(IV) halide : Al halide is 1:4 to 4:1.

8. A process according to claim 1, wherein a mixture of Al halide and Ti(IV) halide is used.

9. A process according to claim 1 wherein at metallic reducing agent is also present.

10. A process according to claim 8 wherein 0.6-1.9 moles of Ti(IV) halide, based on one mole of ferrocene, $(C_5H_4R^3-)$ $Fe(C_5H_4R^1-)$ or $(C_9H_7-)_2Fe$, are used.

11. A process according to claim 10 wherein a metallic reducing agent is also used.

12. A process according to claim 1 wherein a mixture of 0.1-4.0 moles of Al bromide or chloride and 0.7-1.9 moles of Ti(IV) bromide or chloride, based on one mole of ferrocene, $(C_5H_4R^3-)Fe(C_5H_rR^1-)$ or $(C_9H_7-)_2Fe$, is used.

13. A process according to claim 12 wherein a metallic reducing agent is also used.

14. A process according to claim 1 wherein a mixture of 2.0-3.0 moles of $AlCl_3$ and 0.9-1.1 moles of $TiCl_4$ is used together with 0.3-0.4 mole of finely divided Al reducing agent, based on one mole of ferrocene, $(C_5H_4R^3-)Fe(C_5H_4R^1-)$ or $(C_9H_7-)_2Fe$.

15. A process according to claim 1 for simultaneously preparing a compound of formula I and a compound of formula III $$[R\, Fe\, R^2]_q^\oplus X^{q\ominus} \quad (I),$$
$$(I), (R)_2Ti(HAL)_2 \quad (III)$$

in which Hal is a halogen atom and R, $R^2$, X and q are as defined in claim 1 which comprises using a Ti(IV) halide and Al halide mixture containing 0.3–0.7 mole of Ti(IV) halide, based on one mole of ferrocene, $(C_5H_4R^3-)Fe(C_5H_4R^1-)$ or $(C_9H_7-)_2Fe$.

16. A process according to claim 15 wherein a metallic reducing agent is present.

17. A process according to claim 15, wherein a mixture of 0.3–0.7 mole of Ti(IV) bromide or chloride and 0.8–2.0 moles of Al bromide or chloride, based on ferrocene, $(C_5H_4R^3-)Fe(C_5H_4R^1-)$ or $(C_9H_7-)_2Fe$, are used.

18. A process according to claim 17 wherein finely divided Al reducing agent is present.

19. A process according to claim 15 wherein 0.4–0.6 mole of Ti(IV) bromide or chloride and 1.0–1.8 moles of Al bromide or chloride, based on one mole of ferrocene, $(C_5H_4R^3-)Fe(C_5H_4R^1-)$ or $(C_9H_7-)_2Fe$, are used.

20. A process according to claim 19 wherein 0.1–1.0 mole of finely divided Al reducing agent, based on one mole of ferrocene, $(C_5H_4R^3-)Fe(C_5H_4R^1-)$ or $(C_9H_7-)_2Fe$, is present.

21. A process according to claim 15 wherein 0.4–0.6 mole of TiCl$_4$ and 1.2–1.4 mole of AlCl$_3$, based on one mole of ferrocene, $(C_5H_4R^3-)Fe(C_5H_4R^1-)$ or $(C_9H_7-)_2Fe$, are used.

22. A process according to claim 21 wherein 0.15–0.2 mole of finely divided Al reducing agent, based on one mole of ferrocene, $(C_5H_4R^3-)Fe(C_5H_4R^1-)$ or $(C_9H_7-)_2Fe$, is present.

23. A process according to claim 1 wherein 0.1–1.0 mole of matallic reducing agent, based on ferrocene, $(C_5H_4R^3-)Fe(C_5H_4R^1-)$ or $(C_9H_7-)_2Fe$, is used.

24. A process according to claim 1 wherein a metallic reducing agent is present in an amount equivalent to that of the Ti(IV) halide.

25. A process according to claim 15, wherein the reaction mixture is deactivated with acidified water or ice-water after the reaction has ended and
(a) after filtration and phase separation the aqueous phase is extracted with an organic, polar solvent under oxidative conditions or
(b) the deactivated reaction mixture is treated oxidatively.

* * * * *